United States Patent
Huang et al.

(10) Patent No.: US 10,537,524 B2
(45) Date of Patent: Jan. 21, 2020

(54) APIXABAN SOLID COMPOSITION AND PREPARATION METHOD THEREOF

(71) Applicant: SUNSHINE LAKE PHARMA CO., LTD., Dongguan, Guangdong (CN)

(72) Inventors: Qibiao Huang, Dongguan (CN); Xin Huang, Dongguan (CN); Fangfang Huang, Dongguan (CN); Jinsong You, Dongguan (CN); Feng Zhao, Dongguan (CN)

(73) Assignee: NORTH & SOUTH BROTHER PHARMACY INVESTMENT COMPANY LIMITED, Wanchai (HK)

( * ) Notice: Subject to any disclaimer, the term of this patent is extended or adjusted under 35 U.S.C. 154(b) by 15 days.

(21) Appl. No.: 16/069,200

(22) PCT Filed: Jan. 11, 2017

(86) PCT No.: PCT/CN2017/070911
§ 371 (c)(1),
(2) Date: Jul. 11, 2018

(87) PCT Pub. No.: WO2017/121340
PCT Pub. Date: Jul. 20, 2017

(65) Prior Publication Data
US 2019/0022008 A1   Jan. 24, 2019

(30) Foreign Application Priority Data

Jan. 12, 2016  (CN) .......................... 2016 1 0018594

(51) Int. Cl.
| A61K 9/16 | (2006.01) |
| A61K 47/32 | (2006.01) |
| A61K 9/00 | (2006.01) |
| A61P 7/02 | (2006.01) |
| A61K 9/20 | (2006.01) |
| A61K 9/28 | (2006.01) |
| A61K 31/437 | (2006.01) |

(52) U.S. Cl.
CPC .......... *A61K 9/1635* (2013.01); *A61K 9/0053* (2013.01); *A61K 9/1617* (2013.01); *A61K 9/1623* (2013.01); *A61K 9/1652* (2013.01); *A61K 9/1694* (2013.01); *A61K 9/2013* (2013.01); *A61K 9/2018* (2013.01); *A61K 9/2027* (2013.01); *A61K 9/2054* (2013.01); *A61K 9/2077* (2013.01); *A61K 9/2893* (2013.01); *A61K 31/437* (2013.01); *A61K 47/32* (2013.01); *A61P 7/02* (2018.01)

(58) Field of Classification Search
None
See application file for complete search history.

(56) References Cited

U.S. PATENT DOCUMENTS

| 6,967,208 B2 | 11/2005 | Pinto et al. |
| 2012/0087978 A1 | 4/2012 | Nause |
| 2013/0045245 A1 * | 2/2013 | Patel .................... A61K 9/2018 424/400 |

FOREIGN PATENT DOCUMENTS

| CN | 102058889 A | 5/2011 |
| CN | 102908324 A | 2/2013 |
| CN | 103830199 A | 6/2014 |
| CN | 104490834 A | 4/2015 |
| CN | 104523619 A | 4/2015 |
| WO | 2011106478 A2 | 9/2011 |
| WO | 2013174498 A1 | 11/2013 |
| WO | 2015121472 A1 | 8/2015 |
| WO | WO 2017/221209 A1 * | 12/2017 ............... A61K 9/20 |

OTHER PUBLICATIONS

International Search Report of PCT/CN2017/070911, dated Apr. 11, 2017.
Written Opinion of PCT/CN2017/070911, dated Apr. 11, 2017.

* cited by examiner

*Primary Examiner* — Brian J Davis
(74) *Attorney, Agent, or Firm* — Kam Wah Law

(57) ABSTRACT

The present invention provided an apixaban solid composition and a preparation method thereof. The method comprises granulating apixaban by wet granulation, wherein the apixaban has a particle size $D_{90}$ more than 89 μm.

24 Claims, No Drawings

APIXABAN SOLID COMPOSITION AND PREPARATION METHOD THEREOF

CROSS-REFERENCE TO RELATED APPLICATIONS

This is a U.S. national stage application of the International Patent Application No. PCT/CN2017/070911, filed Jan. 11, 2017, which claims priorities to Chinese Patent Application No. 201610018516.8, filed Jan. 12, 2016, and No. 201610018594.8, filed Jan. 12, 2016, all of which are incorporated herein by reference in their entirety.

FIELD OF THE INVENTION

This invention relates to the pharmaceutical formulation field, particularly to an apixaban solid composition and a preparation method thereof.

BACKGROUND OF THE INVENTION

Apixaban (API) is a known compound having the following structure:

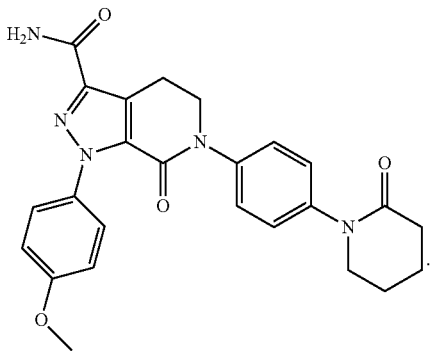 [SMILES: COc1ccc(-n2nc(C(N)=O)c3c2C(=O)N(c2ccc(N4CCCCC4=O)cc2)CC3)cc1]

The chemical name of apixaban is 4,5,6,7-tetrahydro-1-(4-methoxyphenyl)-7-oxo-6-[4-(2-oxopiperdin-1-yl)phenyl-1H-pyrazolo [3,4-c]pyridine-3-carboxamide (CAS name) or 1-(4-methoxyphenyl)-7-oxo-6-[4-(2-oxopiperidin-1-yl)phenyl]-4,5,6,7-tetrahydro-1H-pyrazolo [3,4-c]pyridine-3-carboxamide (IUPAC name).

Apixaban was disclosed in U.S. Pat. No. 6,967,208 and U.S. Patent applications Nos. 2012/0087978 and 2013/0045245, which are herein incorporated by reference in their entireties. Apixaban has utility as a blood coagulation factor Xa inhibitor, and is being developed for oral administration in a variety of indications that require the use of an antithrombotic agent, e.g., surgical operation of the hip or knee of the patient, and preventing death in atrial fibrillation, or using in the treatment of venous thrombosis.

At present, the common methods of improving drug stability and dissolution rate in the pharmaceutical formulation field include the followings: salifying, decreasing particle size, adopting non-aqueous solvent/cosolvent, preparing emulsion or self-microemulsion, inclusion with cyclodextrin, adopting thermodynamically unstable crystalline or preparing solid dispersions, and so on.

However, the pharmaceutical components of apixaban formulations and a preparation method thereof remain to be further studied.

SUMMARY OF THE INVENTION

The application provided herein is based on the following questions and the inventors' discoveries of facts:

The production facilities of the current apixaban tablets in the market are very expensive. The decrease in compressibility of materials is rather high, which lead to a rather high risk in the homogeneity of product, and poor particle compressibility. A formulation prepared by a wet granulation method and a formulation prepared from large particles of apixaban do not have optimal absorption in the body according to the disclosure in U.S. patent application publication 2013/0045245. This may pose a challenge to quality control. Therefore, it has provided apixaban particles having a particle size $D_{90}$ (90% volume) less than 89 μm. This indicates that the drug formulation has a high requirement for the raw materials, which makes the preparation process of the raw materials more complicated.

The present invention provides a novel apixaban solid composition and a preparation method thereof. Surprisingly, the inventors have found that the apixaban solid composition provided herein has a faster dissolution rate and a higher dissolution compared with the prior arts. Further, the product is more stable. Also the inventors have found that the preparation method of the apixaban solid composition provided herein has a simple operation, the product has reliable quality, and the preparation method is more suitable for commercial production.

Based on the above, in a first aspect, provided herein is an apixaban solid composition. According to an embodiment of this invention, the solid composition comprises apixaban having a particle size $D_{90}$ more than 89 μm. Surprisingly, the inventors have found that the restrictions on scale production from small particles of apixaban can be overcome greatly by using apixaban having a particle size $D_{90}$ more than 89 μm, which reduce the cost of production and is suitable for industrial production. Granulated capability and compressibility of the apixaban solid composition disclosed herein are good, the tablet pressing procedure is stable and controllable, and the repeatability of the process is good. More importantly, examples of the apixaban solid composition provided herein have significant advantages including a faster dissolution rate and a higher dissolution compared with prior arts and a more stable product.

According to an embodiment of this invention, the apixaban solid composition further comprises at least one of the following additional technical features.

According to an embodiment of this invention, the apixaban solid composition is obtained by a wet granulation method. The inventors have found that granulated capability and compressibility of the solid composition prepared from a particle size more than 89 μm by a wet granulation method are much better, which results in a faster dissolution rate and a higher dissolution, and a more stable product.

According to an embodiment of this invention, the apixaban solid composition further comprises a binder. The inventors have found that the apixaban solid composition with the binder has better granulated capability and compressibility, and higher repeatability of the process.

According to an embodiment of this invention, the particle size $D_{90}$ of the apixaban is more than 89 μm. For example, according to an embodiment of this invention, the particle size $D_{90}$ of the apixaban is not less than 90 μm, preferably not less than 100 μm, more preferably not less than 150 μm. In addition, according to another an embodiment of this invention, the particle size $D_{90}$ of the apixaban is not more than 550 μm, preferably not more than 400 μm.

According to an embodiment of this invention, the particle size $D_{90}$ of the apixaban is not less than 100 μm and not more than 550 μm. The inventors have found that the dissolution rate and dissolution of the apixaban solid composition, when it is prepared from apixaban having a particle size $D_{90}$ not less than 100 μm and not more than 550 μm and acting in concert with a binder, are higher; and the product is more stable.

According to an embodiment of this invention, the particle size $D_{90}$ of the apixaban is not less than 150 μm and not more than 400 μm. The inventors have found that the apixaban solid composition, when it is prepared from apixaban having a particle size $D_{90}$ not less than 150 μm and not more than 400 μm and acting in concert with a binder, has higher dissolution rate and dissolution; and the product is more stable.

According to an embodiment of this invention, the binder is povidone. The inventors have found that povidone used as a binder can result in the particles having better granulated capability and compressibility; the tablet pressing procedure being more stable and controllable; the repeatability of the process being higher; and the process being more stable.

According to an embodiment of this invention, the binder has a content of 2.0% to 8.0% by weight, based on the total weight of the solid composition. The inventors have found that when the amount of the binder in the solid composition is controlled at 2.0% to 8.0%, the dissolution rate of the product is faster and the dissolution platform is normal.

According to an embodiment of this invention, the binder is provided in dissolved form in an acidic substance or DMSO. The inventors have found that the binder provided in dissolved form in an acidic substance or DMSO is more benefit for dissolution of the apixaban solid composition.

According to an embodiment of this invention, the acidic substance is acetic acid. The inventors have found that when the binder is provided in dissolved form in acetic acid, the dissolution rate of the apixaban solid composition has a significant advantage.

According to an embodiment of this invention, the content of the binder in acetic acid is 0.02 g/mL to 0.5 g/mL. The inventors have found that when the content of the binder in glacial acetic acid is in a range of 0.02 g/mL to 0.5 g/mL, the dissolution rate of the product is faster and the dissolution platform is normal.

According to a specific embodiment of this invention, the apixaban solid composition further comprises a filler, a disintegrant, a surfactant and a lubricant. Surprisingly, the inventors have found that the restrictions on scale production from small particles of apixaban can be overcome greatly by using apixaban having a particle size $D_{90}$ more than 89 μm, and the granulated capability and compressibility can be further promoted when acting in concert with a binder. When further acting in concert with a filler, a disintegrant, a surfactant and a lubricant, the obtained composition is stable, the dissolution rate and the dissolution of which also be promoted.

According to a specific embodiment of this invention, the filler is corn starch, pregelatinized starch, complex starch, lactose anhydrous, lactose monohydrate, microcrystalline cellulose, methylcellulose, hydroxy propyl cellulose, hydroxy propyl methyl cellulose, mannitol, maltitol, inositol, xylitol, lactitol or a combination thereof.

According to a specific embodiment of this invention, the filler is a mixture of lactose anhydrous and microcrystalline cellulose.

According to another specific embodiment of this invention, wherein the lactose anhydrous has a content of 33.50% to 63.50%, and the microcrystalline cellulose has a content of 24.00% to 54.00% by weight, based on the total weight of the solid composition.

According to a specific embodiment of this invention, the disintegrant is croscarmellose sodium.

According to another embodiment of this invention, wherein the disintegrant has a content of 2.00% to 8.00% by weight, based on the total weight of the solid composition.

According to a specific embodiment of this invention, the surfactant is sodium dodecyl sulfate.

According to another specific embodiment of this invention, wherein the surfactant has a content of 0.50% to 4.00% by weight, based on the total weight of the solid composition.

According to a specific embodiment of this invention, the lubricant is magnesium stearate.

According to another specific embodiment of this invention, wherein the lubricant has a content of 0.50% to 2.50% by weight, based on the total weight of the solid composition.

In a second aspect, provided herein is an apixaban solid composition. According to an specific embodiment of this invention, the solid composition disclosed herein comprises 2.50 parts by weight of apixaban, 33.50 to 63.50 parts by weight of lactose anhydrous, 24.00 to 54.00 parts by weight of microcrystalline cellulose, 2.00 to 8.00 parts by weight of croscarmellose sodium, 2.00 to 8.00 parts by weight of povidone, 0.50 to 4.00 parts by weight of sodium dodecyl sulfate and 0.50 to 2.50 parts by weight of magnesium stearate, wherein the apixaban has a particle size $D_{90}$ more than 89 μm. The restrictions on scale production from small particles of apixaban can be overcome greatly by examples of the apixaban solid composition disclosed herein. The granulated capability and compressibility is much better by using 2.50% apixaban and acting in concert with a filler, a disintegrant, a binder, a surfactant and a lubricant. Especially under the effect of the binder, the tablet pressing procedure is more stable and controllable, and the repeatability of the process is higher. The examples of the apixaban solid composition provided herein have significant advantages, which include a simple preparation method suitable for scaled production, a faster dissolution rate and a higher dissolution compared with prior arts; and a more stable product.

According to an embodiment of this invention, the apixaban solid composition further comprises at least one of the following additional technical features:

According to an embodiment of this invention, the particle size $D_{90}$ of the apixaban is not less than 100 μm and not more than 550 μm. The inventors have found that the apixaban solid composition, when it is prepared from the apixaban having a particle size $D_{90}$ not less than 100 μm and not more than 550 μm and acting in concert with a filler, a disintegrant, a binder, a surfactant and a lubricant having the above amount, especially under the effect of the binder having the above amount, has better dissolution rate and dissolution, the product is more stable.

According to an embodiment of this invention, the particle size $D_{90}$ of the apixaban is not less than 150 μm and not more than 400 μm. The inventors have found that the dissolution rate and dissolution of the apixaban solid composition, when it is prepared from apixaban having a particle size $D_{90}$ not less than 150 μm and not more than 400 μm and a filler, a disintegrant, a binder, a surfactant and a lubricant having the above amount, especially under the effect of the binder having the above amount, are much better, the product is more stable.

In a third aspect, provided herein is an apixaban solid composition. According to an embodiment of this invention, the solid composition comprises 2.50% of apixaban, 48.50% of lactose anhydrous, 39.00% of microcrystalline cellulose, 4.00% of croscarmellose sodium, 3.00% of povidone, 2.00% of sodium dodecyl sulfate and 1.00% of magnesium stearate by weight, based on the total weight of the solid composition, wherein the apixaban has a particle size $D_{90}$ more than 89 μM.

In a fourth aspect, provided herein is an apixaban solid composition. According to an embodiment of this invention, the solid composition comprises 2.50% of apixaban, 63.50% of lactose anhydrous, 24.00% of microcrystalline cellulose, 4.00% of croscarmellose sodium, 3.00% of povidone, 2.00% of sodium dodecyl sulfate and 1.00% of magnesium stearate by weight, based on the total weight of the solid composition, wherein the apixaban has a particle size $D_{90}$ more than 89 μM.

In a fifth aspect, provided herein is an apixaban solid composition. According to an embodiment of this invention, the solid composition comprises 2.50% of apixaban, 33.50% of lactose anhydrous, 54.00% of microcrystalline cellulose, 4.00% of croscarmellose sodium, 3.00% of povidone, 2.00% of sodium dodecyl sulfate and 1.00% of magnesium stearate by weight, based on the total weight of the solid composition, wherein the apixaban has a particle size $D_{90}$ more than 89 μm.

In a sixth aspect, provided herein is an apixaban solid composition. According to an embodiment of this invention, the solid composition comprises 2.50% of apixaban, 47.50% of lactose anhydrous, 39.00% of microcrystalline cellulose, 2.00% of croscarmellose sodium, 8.00% of povidone, 0.50% of sodium dodecyl sulfate and 0.50% of magnesium stearate by weight, based on the total weight of the solid composition, wherein the apixaban has a particle size $D_{90}$ more than 89 μM.

In a seventh aspect, provided herein is an apixaban solid composition. According to an embodiment of this invention, the solid composition comprises 2.50% of apixaban, 42.00% of lactose anhydrous, 39.00% of microcrystalline cellulose, 8.00% of croscarmellose sodium, 2.00% of povidone, 4.00% of sodium dodecyl sulfate and 2.50% of magnesium stearate by weight, based on the total weight of the solid composition, wherein the apixaban has a particle size $D_{90}$ more than 89 μM.

According to a specific embodiment of this invention, the above examples of the apixaban solid composition provided herein have significant advantages including a faster dissolution rate and a higher dissolution compared with prior art, and a more stable product.

According to a specific embodiment of this invention, the solid composition may be tablets, capsules or granules. The above dose forms are beneficial for the dissolution of the solid composition in patients and the absorption of the active ingredients.

In the eighth aspect, provided herein is a preparation method of an apixaban composition. According to an embodiment of this invention, the method comprises granulating apixaban by using a wet granulation method to get a binder solution, wherein the apixaban has a particle size $D_{90}$ more than 89 μm. The restrictions on scale production from small particles of apixaban can be overcome greatly by the apixaban solid composition prepared by the method described in the examples disclosed herein. The method disclosed herein is more suitable for industrial scale production, and the granulated capability and compressibility of the composition is much better. The tablet pressing procedure is stable and controllable, the repeatability of the process is good, and the process is stable. The apixaban composition prepared by the method described in the examples disclosed herein has significant advantages, which include a faster dissolution rate and a higher dissolution compared with prior arts, and a more stable product.

According to an embodiment of this invention, the preparation method of the apixaban composition further comprises at least one of the following additional technical features.

According to an embodiment of this invention, the wet granulation method comprises dissolving apixaban and a binder in a wetting agent to get a binder solution. The inventors have found that the apixaban solid composition, when it is prepared by a wet granulation method and acting in concert with a binder, has better granulated capability and compressibility, the repeatability of the process is higher.

According to an embodiment of this invention, the wetting agent is acetic acid or DMSO. The inventors through screening experiment have found that when the wetting agent is acetic acid or DMSO, the dissolution rate of the apixaban solid composition is higher.

According to an embodiment of this invention, the binder is povidone. The inventors have found that povidone used as a binder can result in the particles having better granulated capability and compressibility; the tablet pressing procedure being more stable and controllable; the repeatability of the process being higher; and the process being more stable.

According to an embodiment of this invention, the particle size $D_{90}$ of the apixaban is not less than 100 μm and not more than 550 μm. The inventors have found that when the dissolved apixaban has a particle size not less than 100 μm and not more than 550 μm and when a binder is in a wetting agent, the obtained solid composition has a faster dissolution rate and a higher dissolution, and the product is more stable.

According to an embodiment of this invention, the particle size $D_{90}$ of the apixaban is not less than 150 μm and not more than 400 μm. The inventors have found that when the dissolved apixaban has a particle size not less than 150 μm and not more than 400 μm and when a binder is in a wetting agent, the obtained solid composition has a faster dissolution rate and a higher dissolution, and the product is more stable.

According to a specific embodiment of this invention, the content of the binder in a wetting agent is from 0.02 g/mL to 0.5 g/mL. The inventors have found that when the content of the binder in a wetting agent is from 0.02 g/mL to 0.5 g/mL, the dissolution rate of the product is faster and the dissolution platform is normal.

According to a specific embodiment of this invention, the preparation method of the apixaban composition further comprises: preheating a filler, a disintegrant and a surfactant in a fluid-bed; spraying the binder solution to the preheated product; drying the preheated product sprayed with the binder solution to get dry granules; sizing the dry granules; and blending a lubricant with the sized granules. The inventors have found that the obtained product prepared by the above preparation method has a faster dissolution rate, higher dissolution and higher quality than that prepared by a dry granulation method.

According to a specific embodiment of this invention, the temperature is from 35° C. to 50° C. after preheating. The inventors have found that the homogeneity and compressibility of granules can be ensured under the above spraying conditions. Through the practical investigation, the inventors have found that a temperature lower than 35° C. after preheating will cause the material to be too wet and easy to collapse, and a temperature higher than 50° C. after preheating will cause more fine powder, and worse compressibility.

According to a specific embodiment of this invention, the spraying is carried out under an atomizing pressure from 0.5 to 2.0 bar and at a spray speed from 3.0 to 20.0 g/min. The inventors have found that the homogeneity and compressibility of granules can be ensured under the above spraying conditions. Through a practical investigation, the inventors have found that when the atomization pressure is higher than 2.0 bar, it may easily cause spray drying, worse granulated capability, and irregular fluidization of materials. When the atomization pressure is lower than 0.5 bar, it may result in large droplets and thus coarser particles. When the spray speed is higher than 20.0 g/min, it may result in a wet material, which in turn makes the particles coarser and easier to collapse. When the spray speed is lower than 3.0 g/min, it may result in spray drying and more fine powder in granules.

According to a specific embodiment of this invention, the preparation method of apixaban composition further comprises: pre-blending a filler, a disintegrant and a surfactant in a high shear wet granulator; spraying the binder solution to the pre-blended product to get wet granules; drying the wet granules in an fluid bed to get dry granules; sizing the dry granules; and blending a lubricant with the sized granules. The inventors have found that the obtained product prepared by the above preparation method has a faster dissolution rate, higher dissolution and higher quality than that prepared by a dry granulation method.

According to an embodiment of this invention, the spraying is carried out at a spray speed from 5 to 60 g/min. The inventors have found that when the spray speed is higher than 60 g/min, it may result in ease caking of material under the effect of a binder due to rapid liquid adding rate, and more coarse granules, and worse compressibility. Also the content uniformity of the product will be affected. When the spray speed is lower than 5 g/min, it may result in too slow liquid adding rate. Further, the wettability of materials may be affected, and more fine powder is in granules, the compressibility is worse, and the content uniformity of the product will be affected, the liquid adding time will be prolong due to too slow spray speed, and the efficiency of production will be affected. Therefore, the spray speed controlled at a range from 5 to 60 g/min will further improve granulated capability and compressibility, and the granulation efficiency will be further improved.

According to an embodiment of this invention, the method further comprises compressing the blend product into tablets and coating the tablets. The compressing treatment can avoid immediately contact of the composition with the gastrointestinal tract, and thus a reduction in its efficacy. The coating treatment can effectively isolate the composition from the air, prevent moisture and avoid light, and further improve the stability of the product.

In a ninth aspect, provided herein is a preparation method of apixaban composition. According to an embodiment of this invention, the method comprises: (1) dissolving apixaban and a binder in a wetting agent to get a binder solution, wherein the apixaban has a particle size $D_{90}$ more than 89 μm, wherein the wetting agent is acetic acid or DMSO, wherein the binder is povidone, and wherein the content of the binder in the wetting agent is 0.02 g/mL to 0.5 g/mL; (2) pre-heating a filler, a disintegrant and a surfactant in a fluid-bed, wherein the temperature is from 35° C. to 50° C. after pre-heating; (3) spraying the binder solution to the preheated product, wherein the spraying is carried out under an atomizing pressure of 0.5 to 2.0 bar and at a spray speed of 3.0 to 20.0 g/min, drying the preheated product sprayed with the binder solution to get dry granules; (4) sizing the dry granules; (5) blending a lubricant with the sized granules; and (6) compressing and coating the blended product. The restrictions on scale production from small particles of apixaban can be overcome greatly by the apixaban solid composition prepared by the method described in the examples disclosed herein. The method is more suitable for industrial scale production. The granulated capability and compressibility of the composition is much better. The tablet pressing procedure is stable and controllable. The repeatability of the process is good. The process is stable. The apixaban composition prepared by the method described in the examples disclosed herein has significant advantages, which include a faster dissolution rate and a higher dissolution compared with prior arts, and a more stable product.

In a tenth aspect, provided herein is a preparation method of apixaban composition. According to an embodiment of this invention, the method comprises: (1) dissolving apixaban and a binder in a wetting agent to get a binder solution, wherein the apixaban has a particle size $D_{90}$ more than 89 μm, wherein the wetting agent is acetic acid or DMSO, wherein the binder is povidone, and wherein the content of the binder in the wetting agent is from 0.02 g/mL to 0.5 g/mL; (2) pre-blending a filler, a disintegrant and a surfactant in a high shear wet granulator; (3) spraying the binder solution to the pre-blended product, wherein the spraying is carried out at a spray speed from 5 to 60 g/min, granulating the pre-blended product sprayed with the binder solution for a time period from 3 to 5 minutes to get wet granules; (4) drying the wet granules in a fluid-bed to get dry granules; (5) sizing the dry granules; (6) blending a lubricant with the sized granules; and (7) compressing and coating the blended product. The restrictions on scale production from small particles of apixaban can be overcome greatly by the apixaban solid composition prepared by the method described in the examples disclosed herein. The method is more suitable for industrial scale production. The granulated capability and compressibility of the composition is much better. The tablet pressing procedure is stable and controllable. The repeatability of the process is good. The process is stable. The apixaban composition prepared by the method described in the examples disclosed herein has significant advantages, which include a faster dissolution rate and a higher dissolution compared with prior art, and a more stable product.

Additional aspects and advantages of the invention will partly be presented in the following description, partly become apparent in the following description or be appreciated in practicing of the invention.

EXAMPLES

Unless defined otherwise, all technical and scientific terms used herein have the same meaning as is commonly understood by one skilled in the art to which this invention belongs. All patents and publications referred to herein are incorporated by reference in their entirety.

The term "comprising" or "comprise" is meant to be open ended, including the indicated component but not excluding other elements.

In the above description, all numbers disclosed herein are approximate values, regardless whether the word "about" is used in connection therewith. The value of each number may differ by below 10% or 1%, 2%, 3%, 4% or 5% reasonable for the persons skilled in the art.

$D_{90}$, i.e., 90% of cumulative volume particle size distribution number, refers to 90% of the sample has the corresponding particle size or smaller. The particle size distribution of the invention can be determined by laser diffraction. The particle size distribution of the raw material apixaban is measured by using a Mastersizer 2000 Malvern laser particle size analyzer in the following examples. An appropriate amount of the test sample is taken into the automatic dry sampler, the measurement is performed 3 times in parallel and the results are averaged.

Apixaban Solid Composition

In one aspect, an apixaban pharmaceutical composition provided herein comprises apixaban and optionally a filler, disintegrant, binder, surfactant and lubricant, wherein apixaban has a particle size $D_{90}$ more than 89 μm. Surprisingly, the inventors have found that the restrictions on scale production from small particles of apixaban can be overcome greatly by using apixaban having a particle size $D_{90}$ more than 89 μm, and the granulated capability and compressibility are much better when acting in concert with a binder. The tablet pressing procedure is stable and controllable. The repeatability of the process is good. More importantly, the examples of the apixaban solid composition provided herein have a faster dissolution rate and a higher dissolution compared with prior arts, and the product is more stable.

According to an embodiment of this invention, the particle size $D_{90}$ of API apixaban is more than 89 μm. In one specific embodiment of this invention, the particle size $D_{90}$ of API apixaban is more than and equal to 100 μm and not more than 550 μm. In another specific embodiment, the particle size $D_{90}$ of API apixaban is more than and equal to 150 μm and not more than 400 μm. In still another specific embodiment, the particle size $D_{90}$ of API apixaban is equal to 100 μm, 150 μm, 200 μm or 300 μm.

According to a specific embodiment of this invention, wherein the apixaban solid composition further comprises a filler, a disintegrant, a surfactant and a lubricant.

In one embodiment, the filler is corn starch, pregelatinized starch, complex starch, lactose anhydrous, lactose monohydrate, microcrystalline cellulose, methylcellulose, hydroxy propyl cellulose, hydroxy propyl methyl cellulose, mannitol, maltitol, inositol, xylitol, lactitol or a combination thereof. Preferably, the filler is a mixture of lactose anhydrous and microcrystalline cellulose. More preferably, the filler is a mixture of lactose anhydrous DCL-21AN and microcrystalline cellulose PH 101. When the lactose anhydrous has a content of 33.50% to 63.50% and the microcrystalline cellulose has a content of 24.00% to 54.00% by weight, the product has an optimal quality.

In another embodiment, the binder is preglatinized gelatin, povidone, methylcellulose, ethyl cellulose, hydroxypropyl methyl cellulose, sodium carboxymethyl cellulose, sugar powder, starch slurry, gelatin or a combination thereof. Preferably the binder is povidone. More preferably the binder is povidone K29/32. When the binder has a content of 2.00% to 8.00% by weight, the product has an optimal quality.

In another embodiment, the disintegrant is sodium starch glycolate, polyvinylpolypyrrolidone, croscarmellose sodium, cross-linked sodium starch glycolate, low-substituted hydroxypropyl cellulose or a combination thereof. Preferably the disintegrant is croscarmellose sodium. When the disintegrant has a content of 2.00% to 8.00% by weight, the product has an optimal quality.

In another embodiment, the surfactant is sodium dodecyl sulfate, sodium dodecyl sulfonate, tween, span or a combination thereof. Preferably the surfactant is sodium dodecyl sulfate. When the surfactant has a content of 0.50% to 4.00% by weight, the product has an optimal quality.

In another embodiment, the lubricant is stearic acid, magnesium stearate, calcium stearate, zinc stearate, glyceryl palmitoyl stearate, sodium stearyl fumarate, low erucic acid rapeseed oil, hydrogenated vegetable oil, mineral oil, sodium dodecyl sulfate, magnesium oxide, silicon dioxide, silicone oil, polyethylene glycol, polyvinyl alcohol, sodium phenylacid, talcor, or a combination thereof. Preferably the lubricant is magnesium stearate. When the lubricant has a content of 0.50% to 2.50% by weight, the product has an optimal quality.

In another aspect, provided herein is an apixaban solid composition comprising 2.50 parts by weight of apixaban, 33.50 to 63.50 parts by weight of lactose anhydrous, 24.00 to 54.00 parts by weight of microcrystalline cellulose, 2.00 to 8.00 parts by weight of croscarmellose sodium, 2.00 to 8.00 parts by weight of povidone, 0.50 to 4.00 parts by weight of sodium dodecyl sulfate and 0.50 to 2.50 parts by weight of magnesium stearate, wherein the apixaban has a particle size $D_{90}$ more than 89 μm. In other words, the apixaban solid composition comprises 2.50% of apixaban, 33.50% to 63.50% of lactose anhydrous, 24.00% to 54.00% of microcrystalline cellulose, 2.00% to 8.00% of croscarmellose sodium, 2.00% to 8.00% of povidone, 0.50% to 4.00% of sodium dodecyl sulfate and 0.50% to 2.50% of magnesium stearate by weight, based on the total weight of the solid composition, wherein the apixaban has a particle size $D_{90}$ more than 89 μm.

In one embodiment, the solid composition comprises 2.50% of apixaban, 48.50% of lactose anhydrous, 39.00% of microcrystalline cellulose, 4.00% of croscarmellose sodium, 3.00% of povidone, 2.00% of sodium dodecyl sulfate and 1.00% of magnesium stearate.

In another embodiment, the solid composition comprises 2.50% of apixaban, 63.50% of lactose anhydrous, 24.00% of microcrystalline cellulose, 4.00% of croscarmellose sodium, 3.00% of povidone, 2.00% of sodium dodecyl sulfate and 1.00% of magnesium stearate.

In another embodiment, the solid composition comprises 2.50% of apixaban, 33.50% of lactose anhydrous, 54.00% of microcrystalline cellulose, 4.00% of croscarmellose sodium, 3.00% of povidone, 2.00% of sodium dodecyl sulfate and 1.00% of magnesium stearate.

In another embodiment, the solid composition comprises 2.50% of apixaban, 47.50% of lactose anhydrous, 39.00% of microcrystalline cellulose, 2.00% of croscarmellose sodium, 8.00% of povidone, 0.50% of sodium dodecyl sulfate and 0.50% of magnesium stearate.

In another embodiment, the solid composition comprises 2.50% of apixaban, 42.00% of lactose anhydrous, 39.00% of microcrystalline cellulose, 8.00% of croscarmellose sodium, 2.00% of povidone, 4.00% of sodium dodecyl sulfate and 2.50% of magnesium stearate.

The dose forms of the apixaban solid composition disclosed herein are tablets, capsules or granules.

The apixaban solid composition disclosed herein has a good stablility and a good uniformity of content, which can improve medication safety effectively. Further, the composition has a fast dissolution rate, which can effectively increase the dissolution and absorption of drugs.

The apixaban solid composition disclosed herein differs from the formulations of original research or other generic pharmaceutical companies. The raw material has a particle size more than 89 μm, therefore, it can greatly overcome the restrictions on scale production from small particles of apixaban, and simplify the preparation process of the raw material. The method is more suitable for industrial scale production.

Preparation Method of Apixaban Composition

In still another aspect, provided herein is a preparation method of an apixaban composition. According to an embodiment of this invention, the method comprises: granulating apixaban by using a wet granulation method, wherein the apixaban has a particle size $D_{90}$ more than 89 μm. According to an embodiment of this invention, the wet granulation method comprises dissolving apixaban and a binder in a wetting agent to get a binder solution. The restrictions on scale production from small particles of apixaban can be overcome greatly by the apixaban solid composition prepared by the method described in the examples disclosed herein. The method is more suitable for industrial scale production, and the granulated capability and compressibility of the composition is much better. The tablet pressing procedure is stable and controllable. The repeatability of the process is good. The process is stable. The apixaban composition prepared by the method described in the examples disclosed herein has significant advantages, which include a faster dissolution rate and a higher dissolution compared with prior art, and a more stable product.

In one specific embodiment of this invention, the wetting agent is acetic acid or DMSO. In another specific embodiment of this invention, the binder may be povidone.

In another specific embodiment of this invention, the ratio of the binder to the wetting agent is from 0.02 g/mL to 0.5 g/mL.

Furthermore, the method of the invention comprises:

(1) dissolving apixaban and a binder in a wetting agent to get a binder solution;

(2) preheating a filler, a disintegrant and a surfactant in a fluid bed to the set material temperature, and spraying the above binder solution, drying after spraying to get dry granules;

(3) sizing the obtained dry granules;

(4) blending a lubricant with the sized granules.

In one embodiment, the material temperature in step (2) is from 35° C. to 50° C.

In another embodiment, the atomization pressure is adjusted at a range from 0.5 to 2.0 bar, the spray speed is from 3.0 to 20.0 g/min in step (2).

In another embodiment, step (2) can be replaced by:

(2-1) pre-blending a filler, a disintegrant and a surfactant in a high shear wet granulator, spraying the above binder solution to get wet granules;

(2-2) drying the wet granules in a fluid-bed.

Furthermore, the method of the invention also comprises step two steps of (5) compressing and (6) coating.

In another embodiment, the filler is corn starch, pregelatinized starch, complex starch, lactose anhydrous, lactose monohydrate, microcrystalline cellulose, methylcellulose, hydroxy propyl cellulose, hydroxy propyl methyl cellulose, mannitol, maltitol, inositol, xylitol, lactitol or a combination thereof.

In another embodiment, the disintegrant is sodium starch glycolate, polyvinylpolypyrrolidone, croscarmellose sodium, cross-linked sodium starch glycolate, low-substituted hydroxypropyl cellulose or a combination thereof.

In another embodiment, the surfactant is sodium dodecyl sulfate, sodium dodecyl sulfonate, tween, span or a combination thereof.

In another embodiment, the lubricant is stearic acid, magnesium stearate, calcium stearate, zinc stearate, glyceryl palmitoyl stearate, sodium stearyl fumarate, low erucic acid rapeseed oil, hydrogenated vegetable oil, mineral oil, sodium dodecyl sulfate, magnesium oxide, silicon dioxide, silicone oil, polyethylene glycol, polyvinyl alcohol, sodium phenylacid, talc or a combination thereof.

The examples of the invention are described in detail. The embodiments described below are exemplary, which are merely to explain the present invention, and not to limit the scope of the present invention. In the examples described below, unless otherwise indicated all temperatures are set forth in degrees Celsius. In test methods without specific conditions in the embodiments, the conditions described in the references in this art or the conditions recommended by the product specification are generally used. The reagents or instruments used herein without marking the manufacturer all are conventional products purchased through the market.

The following abbreviations are used throughout the specification:

g gram mL milliliter

μL microlitre h hour, hours min minute, minutes s second

Content of each component of formulations 1 to 13 in Examples 1 to 5 is as shown in table 1.

TABLE 1

|  | Amount per formulation unit (mg) | Percentage per formulation unit (%) |
|---|---|---|
| Core tablet: | | |
| Apixaban | 5 | 2.5 |
| Lactose anhydrous | 97 | 48.5 |
| Microcrystalline cellulose | 78 | 39 |
| Croscarmellose sodium | 8 | 4 |
| Povidone | 6 | 3 |
| Sodium dodecyl sulfate | 4 | 2 |
| Magnesium stearate | 2 | 1 |
| Total | 200 | 100 |
| Coating | | |
| Opadry Y-1-7000 | 6 | 3 |

Example 1. Study on Granulation Process

In this example, the inventors studied an effect of the granulation process on the rate of dissolution of the formulations under a condition of apixaban having a particle size $D_{90}$ 300 μm. Wherein the particle size of API, wetting agent and granulating process of formulations 1 to 3 are listed in table 2.

TABLE 2

| Formulation | Particle size (μm) | Wetting agent | Povidone/ Wetting agent (g/mL) | Granulation process |
|---|---|---|---|---|
| Formulation 1 | 300 | No | 0 | Dry granulation |
| Formulation 2 | 300 | Acetic acid | 0.2 | Fluidized bed wet granulation |
| Formulation 3 | 300 | Acetic acid | 0.2 | High shear wet granulation |

1. Preparation Method of Formulation 1

(1) weighing: precisely weighing the components according above formulation;

(2) sieving: sieving the materials other than magnesium stearate with a screen model 032R at a rotation rate of 1440 rpm;

(3) blending 1: blending the sieved materials from the step (2) in a mixing drum at a rotation rate of 10 rpm for 10 min;

(4) blending 2: sieving an intragranular magnesium stearate through a #30 mesh, and adding the sieved magnesium stearate to the mix from step (3) and blending at a rotation rate of 10 rpm for 5 min;

(5) granulating: granulating the mix from step (4) using a dry granulation after adjusting the parameters. The key process parameters were set as follows: horizontal screw speed was 10-30 rpm, vertical screw speed was 250 rpm, pressure roller speed was 6 rpm, pressure of pressure roller was 20-30 bar, interval of pressure roller was 2 mm, and shredding speed was 2000 rpm, adopting pressure roller with horizontal and shallow stripes and using screen model 0065;

(6) blending total: sieving an extra-granular magnesium stearate through a #30 mesh, and adding the sieved magnesium stearate to the mix from step (5) and blending at a rotation rate of 10 rpm for 5 min;

(7) compressing: compressing the blended granules from step (6) into tablets with a weight of 200 mg and a target hardness of 90 N;

(8) coating: coating the core tablet from step (7) with 3.0% of mass addition of a coating material.

2. Preparation Method of Formulation 2

(1) weighing: precisely weighing the components according to table 1;

(2) preparing a binder: weighing the wetting agent according to the amount of povidone/wetting agent listed in table 2, dissolving the weighted apixaban and povidone in acetic acid, stirring until homogeneous for use;

(3) granulating: pre-heating lactose anhydrous, microcrystalline cellulose, croscarmellose sodium, sodium lauryl sulfate in a fluid bed, spraying the binder from step (2), and granulating. The atomization pressure is 0.7 Bar, the spray speed is 7 g/min, the materials temperature is 42° C., the air flow and inlet air temperature are set up according to incipient fluidization and temperature of the materials;

(4) sizing: sizing the dry granules from step (3) with a screen model 032R;

(5) blending total: blending an extra-granular magnesium stearate with the granules from step (4) at a rotation rate of 10 rpm for 5 min;

(6) compressing: compressing the blended granules from step (5) into tablets with a weight of 200 mg and a target hardness of 90 N;

(7) coating: coating the core tablet from step (6) with 3.0% of mass addition of coating material.

3. Preparation Method of Formulation 3

(1) weighing: precisely weighing the components according to table 1;

(2) preparing a binder: weighing the wetting agent according to the amount of povidone/wetting agent listed in table 2, dissolving the weighted apixaban and povidone in glacial acetic acid, stirring until homogeneous for use;

(3) granulating: pre-blending lactose anhydrous, microcrystalline cellulose, croscarmellose sodium, sodium lauryl sulfate in a high shear wet granulator, spraying the binder from step (2) at a spray speed of 5-60 g/min, and after spraying, granulating for 3 min.

(4) drying: drying the wet granules from step (3) in a fluid bed, the final temperature of the dry granules is controlled at 50° C., LOD is controlled below 2%;

(5) sizing: sizing the dry granules from step (4) with a screen model 032R;

(6) blending total: blending an extra-granular magnesium stearate with the granules from step (5) at a rotation rate of 10 rpm for 5 min;

(7) compressing: compressing the blended granules from step (6) into tablets with a weight of 200 mg and a target hardness of 90 N;

(8) coating: coating the core tablet from step (7) with 3.0% of mass addition of coating material.

4. Dissolution Curve

Dissolution Conditions

Method: paddle method at 75 rpm;

Dissolution medium: pH 6.8 phosphate buffer with 0.05% sodium dodecyl sulfate (SDS), 900±9 mL (degassing prior to use by using a DISTEK dissolution media degas ser at 37° C.);

Medium temperature: 37.0±0.5° C.;

Sampling time: 5, 10, 15, 20, 30, 45, 60 min;

Sampling volume: 2 mL;

Sampling position: the central position from the top of the blade to the liquid surface and 10 mm away from the inner wall of the dissolution cup.

Chromatographic Conditions

Instrument: HPLC

Detection wavelength: UV 280 nm

Chromatographic column: Agilent ZORBAX RX-C8, 4.6 mm×150 mm, 5 μm or Welch Ultimate XB-C8, 4.6 mm×150 mm, 5 μm Mobile phase: (0.01 mol/L potassium dihydrogen phosphate solution, adjusting pH to 3.8 with phosphoric acid)-acetonitrile (60:40)

Column temperature: 25° C.

Flow rate: 1.0 mL/min

Sample volume: 80 μL

Run time: 6 min (about 1.5 times of the retention time of apixaban)

Wherein the dissolution curves (%) of formulations 1 to 3 are listed in table 3.

TABLE 3 the dissolution curves (%) of formulations 1 to 3

| Formulation | 5 min | 10 min | 15 min | 20 min | 30 min | 45 min | 60 min |
| --- | --- | --- | --- | --- | --- | --- | --- |
| Formulation 1 | 12 | 18 | 23 | 28 | 31 | 32 | 32 |
| Formulation 2 | 37 | 82 | 93 | 98 | 100 | 101 | 101 |
| Formulation 3 | 33 | 64 | 90 | 93 | 97 | 99 | 100 |

Conclusion: The formulation 2 and formulation 3 were granulated by using a fluid bed wet granulation and high shear wet granulation respectively, it can be seen from the data listed in the table that the dissolution rate is obviously faster than formulation 1, more than 90% at 15 min, and the dissolution platform reached near 100%. Therefore the wet granulation is a suitable method having the best effect.

Example 2. Study on Various Wetting Agents

In this example, the inventors studied an effect of the types of wetting agents on the rate of dissolution of the formulations under the condition of apixaban having a particle size $D_{90}$ 92 μm. The particle size of API, wetting agent and granulating process of formulations 4 to 6 are listed in Table 4.

TABLE 4

| Formulation | Particle size (μm) | Wetting agent | Povidone/Wetting agent (g/mL) | Granulation process |
|---|---|---|---|---|
| Formulation 4 | 92 | water | 0.2 | Fluidized bed wet granulation |
| Formulation 5 | 92 | ethanol | 0.2 | Fluidized bed wet granulation |
| Formulation 6 | 92 | glacial acetic acid | 0.2 | Fluidized bed wet granulation |

1. Preparation Method of Formulations 4 to 6

(1) weighing: precisely weighing the components according to Table 1;

(2) preparing a binder: weighing water, ethanol or glacial acetic acid according to the amount of povidone/wetting agent listed in table 4, dissolving the weighted apixaban and povidone in the wetting agent, stirring for use.

The next steps are the same as steps (3) to (7) of the preparation method of formulation 2.

2. Dissolution Curve

Dissolution conditions were the same as those of Example 1

Wherein the dissolution curves (%) of formulations 4 to 6 are listed in table 5,

TABLE 5

The dissolution curves (%) of formulations 4 to 6.

| Formulation | 5 min | 10 min | 15 min | 20 min | 30 min | 45 min | 60 min |
|---|---|---|---|---|---|---|---|
| Formulation 4 | 9 | 17 | 23 | 28 | 35 | 41 | 41 |
| Formulation 5 | 8 | 15 | 22 | 27 | 34 | 39 | 40 |
| Formulation 6 | 34 | 82 | 91 | 98 | 99 | 100 | 100 |

Conclusion: from the formulations 4 to 6 granulated by a fluidized bed granulation, the dissolution rate of formulation 6 is obviously faster than formulation 4 and formulation 5 by using glacial acetic acid as a wetting agent, the dissolution platform reached near 100%; therefore, the dissolution reached 90% at 15 min by using glacial acetic acid as a wetting agent, and the dissolution platform is normal, and reached near 100%, so glacial acetic acid as a wetting agent was used herein to reach the best effect.

At the same time, the inventors also studied the dissolution rate of the composition using DMSO as a wetting agent, the inventors discovered that the composition adopting either DMSO or glacial acetic acid as wetting agent has a fast dissolution rate.

Example 3. Study on Amount of Wetting Agents

In this example, the inventors studied an effect of the ratio of povidone/glacial acetic acid on the rate of dissolution of the formulations under the condition of apixaban having a particle size $D_{90}$ 150 μm. Wherein the particle size of API, wetting agent and granulating process of formulations 7 to 11 are listed in table 6.

TABLE 6

| Formulation | Particle size (μm) | Povidone/glacial acetic acid (g/mL) | Granulation process |
|---|---|---|---|
| Formulation 7 | 150 | 0.1 | Fluidized bed wet granulation |
| Formulation 8 | 150 | 0.2 | Fluidized bed wet granulation |
| Formulation 9 | 150 | 0.3 | Fluidized bed wet granulation |
| Formulation 10 | 150 | 0.02 | Fluidized bed wet granulation |
| Formulation 11 | 150 | 0.5 | Fluidized bed wet granulation |

1. Preparation Method of Formulations 7 to 11

(1) weighing: precisely weighing the components according to table 1;

(2) preparing a binder: weighing glacial acetic acid according to the amount of povidone/glacial acetic acid listed in table 6, dissolving the weighted apixaban and povidone in acetic acid, stirring until homogeneous for use;

The next steps are the same as steps (3) to (7) of the preparation method of formulation 2.

3. Dissolution Curve

Dissolution conditions were the same as those of Example 1

Wherein the dissolution curves (%) of formulations 7 to 11 are listed in table 7,

TABLE 7 the dissolution curves (%) of formulations 7 to 11.

| Formulation | 5 min | 10 min | 15 min | 20 min | 30 min | 45 min | 60 min |
|---|---|---|---|---|---|---|---|
| Formulation 7 | 36 | 79 | 92 | 98 | 100 | 101 | 100 |
| Formulation 8 | 38 | 81 | 94 | 98 | 98 | 99 | 98 |
| Formulation 9 | 35 | 79 | 90 | 95 | 98 | 100 | 101 |
| Formulation 10 | 40 | 83 | 97 | 99 | 100 | 101 | 101 |
| Formulation 11 | 34 | 77 | 88 | 94 | 97 | 99 | 99 |

Conclusion: from the results of dissolution of formulations 7 to 11, they have the similar dissolution curve, the dissolution all reached more than 85% at 15 min, and the dissolution platform is normal, reached near 100%, so the amount of a binder in the wetting agent between 0.02 and 0.5 g/mL was used in the product, the product has a faster dissolution rate and a normal dissolution platform, it meets quality standards. In addition, the inventors discovered that the concentration of a binder in the wetting agent lower than 0.02 g/mL would lead to an excessive amount of the binder solution, a longer granulating time, time and energy consuming, which is not suitable for industrial production, although the binder with the concentration lower than 0.02 g/mL does not affect the quality of the product; if the binder has a concentration higher than 0.5 g/mL, it is limited by binders, such as the solution of povidone (PVP), in such a situation, parts of binder, such as PVP, cannot be dissolving and in a suspension state.

Example 4. Study on Particle Size of API

1. Investigation of the Effect of API Particle Size on Materials Costs

API in the apixaban solid composition provided in the application is apixaban having a particle size $D_{90}$ more than 89 μm. If adopting the apixaban having a particle size $D_{90}$ less than or equal to 89 μm in apixaban solid composition, apixaban need to be ground, in this case, the materials cost will increase greatly, it is embodied in the following aspects: first, it is need to purchase a grinder, and an universal grinder will be chose in generally, which is very expensive; if materials having a very small particle size (less than or equal to 10 μm) is needed, an airflow pulverizer will be chose to micronize, which is more expensive. Second, the raw materials will be lost greatly during the grinding process, the yield is usually between 80% and 90%, and after grinding, a full analysis should be performed for release and the stability should be evaluated, which will consume more raw materials, so the cost will increase significantly. Third, the grinding process will consume much water, electricity and gas, the energy consumption is too high, and the process operation needs multiple persons to carry out, and much time will be consumed in installation equipment and cleaning equipment, therefore more manpower and material resources will be required. Finally, the ground raw materials easily agglomerate, which should be ground for immediate use, therefore it is not good for commercialized continuous production. Loss rate of API having various particle sizes in grinding process were listed in table 8.

TABLE 8

| Particle size before grinding | Particle size after grinding | Type of grinder | Loss rate of the raw materials |
|---|---|---|---|
| 360 | 58 | Universal grinder | 10% |
| 360 | 8 | Airflow pulverizer | 18% |
| 150 | 30 | Universal grinder | 13% |
| 150 | 4 | Airflow pulverizer | 20% |

2.88 kg of apixaban was consumed in the preparation procedure of each batch product used for register, if the particle size of the raw materials for the production of drugs was between 10 and 89 μm, an universal grinder was required to be used first, and the loss rate of the raw materials was at least 10%, so extra amount of the raw materials was at least 0.32 kg; and sampling and detection were needed in the grinding procedure, and an appropriate amount of sample was retained, so additional extra amount of the raw materials was 0.1 kg to 0.5 kg (each grind can provide the amount of 1 to 5 batches, 0.5 kg sample was retained at each grind), if including the energy consumption and manpower consumption, the cost of the raw materials will increase 17% to 31% at least, without the depreciation of equipment. Similarly, if the particle size of the raw materials is less than 10 μm, the cost of the raw materials will increase 28% to 42%. Therefore, it is great cost advantage that adapixaban having a particle size $D_{90}$ more than 89 μm was adopted as the raw material for granulation.

2. Investigation of the Effect of API Particle Size on Dissolution Rate

In this example, the inventors researched the effect of API particle size on dissolution under a condition of 0.2 g/mL povidone/glacial acetic acid.

TABLE 9

The particle size of API, wetting agent and granulating process of formulations 2, 3, 6, 8, 12 and 13.

| Formulation | Particle size (μm) | Povidone/glacial acetic acid (g/mL) | Granulation process |
|---|---|---|---|
| Formulation 2 | 300 | 0.2 | Fluidized bed wet granulation |
| Formulation 3 | 300 | 0.2 | High shear wet granulation |

TABLE 9-continued

The particle size of API, wetting agent and granulating process of formulations 2, 3, 6, 8, 12 and 13.

| Formulation | Particle size (μm) | Povidone/glacial acetic acid (g/mL) | Granulation process |
|---|---|---|---|
| Formulation 6 | 92 | 0.2 | Fluidized bed wet granulation |
| Formulation 8 | 150 | 0.2 | Fluidized bed wet granulation |
| Formulation 12 | 200 | 0.2 | Fluidized bed wet granulation |
| Formulation 13 | 360 | 0.2 | High shear wet granulation |

The preparation procedure of formulations 12 and 13 were described as follows:

(1) weighing: precisely weighing the components according to table 1;

(2) preparing a binder: weighing glacial acetic acid according to the amount of povidone/glacial acetic acid listed in table 9, dissolving the weighted apixaban and povidone in acetic acid, stirring until homogeneous for use;

The next steps are the same as steps (3) to (7) of the preparation method of formulation 2 or steps (3) to (8) of the preparation method of formulation 3.

Dissolution conditions were the same as those of Example 1.

Wherein the dissolution curves (%) of formulations 2, 3, 6, 8, 12 and 13 are listed in table 10,

TABLE 10

The dissolution curves (%) of formulations 2, 3, 6, 8, 12 and 13.

| Formulation | 5 min | 10 min | 15 min | 20 min | 30 min | 45 min | 60 min |
|---|---|---|---|---|---|---|---|
| Formulation 2 | 37 | 82 | 93 | 98 | 100 | 101 | 101 |
| Formulation 3 | 33 | 64 | 90 | 93 | 97 | 99 | 100 |
| Formulation 6 | 34 | 82 | 91 | 98 | 99 | 100 | 100 |
| Formulation 8 | 36 | 79 | 92 | 98 | 100 | 101 | 100 |
| Formulation 12 | 39 | 85 | 97 | 98 | 98 | 99 | 98 |
| Formulation 13 | 36 | 83 | 93 | 96 | 98 | 99 | 99 |

From table 10, the product has a fast dissolution rate under the condition of API having a particle size $D_{90}$ more than 89 μm, no matter by wet granulation or fluidized bed granulation process, the dissolution platform reached 100%.

Example 5 Investigation of Stability

In this example, the inventors researched stability of the apixaban composition prepared by the method of the examples disclosed herein, as described in the following methods:

Apixaban film-coated tables with 2 g silica gel desiccant were packed using a HDPE bottle, 60 tablets per bottle, and accelerated stability test was carried out at 40° C./75% RH, the content, relative substance and dissolution were detected by sampling at 0 day, 1 month, 2 months, 3 months.

The apixaban tablets were extracted with acetonitrile-ultra pure water (50:50) after treating, high performance liquid chromatography was used for detection, and an external standard method was used for calculated based on the principal component analysis. Dissolution was measured by USP the first paddle method, high performance liquid chromatography was used for detection, and an external standard method was used for calculated based on the principal component analysis. And the content of apixaban in apixaban tablets after treating and the content of the relative substances were obtained.

Content of Apixaban

Chromatographic Conditions

Apparatus: high performance liquid chromatograph (UV detector);

Chromatographic column: Agilent ZORBAX RX-C8, 250 mm×4.6 mm, 5 μm

Detection wavelength: 280 nm
Flow rate: 1.0 mL/min
Column temperature: 25° C.
Sample volume: 15 μL
Run time: 10 min (about 1.5 times of the retention time of apixaban)

Content of the Relative Substances

Chromatographic Conditions

Apparatus: high performance liquid chromatograph (UV detector);

Chromatographic column: Agilent ZORBAX RX-C8, 4.6 mm×250 mm, 5 μm

Detection wavelength: 280 nm
Flow rate: 1.0 mL/min
Column temperature: 20° C.
Sample volume: 10 μL
Run time: 48 min Wherein the content of apixaban of formulations 2, 3, 6, 8, 12 and 13 were listed in table 10, and the content of the relative substances of formulations 2, 3, 6, 8, 12 and 13 were listed in table 11.

TABLE 10

| Formulation | 0 month (%) | 1 month (%) | 2 months (%) | 3 months (%) |
| --- | --- | --- | --- | --- |
| Formulation 2 | 100 | 100.5 | 100.3 | 100.7 |
| Formulation 3 | 99.3 | 99.6 | 100.5 | 100.1 |
| Formulation 6 | 99.5 | 99.9 | 99.3 | 99.6 |
| Formulation 8 | 99.2 | 98.4 | 98.3 | 99.5 |
| Formulation 12 | 97.8 | 98.7 | 99.3 | 99.0 |
| Formulation 13 | 99.1 | 100.2 | 99.3 | 99.5 |

TABLE 11

| Formulation | Impurities | 0 month (%) | 1 month (%) | 2 months (%) | 3 months (%) |
| --- | --- | --- | --- | --- | --- |
| Formulation 2 | RRT = 0.54 | <LOQ | <LOQ | <LOQ | <LOQ |
|  | RRT = 0.71 | <LOQ | <LOQ | <LOQ | 0.05 |
|  | RRT = 1.20 | ND | <LOQ | 0.05 | 0.05 |
|  | RRT = 1.49 | 0.05 | 0.06 | 0.05 | 0.06 |
|  | RRT = 1.70 | ND | ND | <LOQ | <LOQ |
|  | Total impurity | 0.05 | 0.06 | 0.10 | 0.16 |
| Formulation 3 | RRT = 0.54 | ND | <LOQ | <LOQ | <LOQ |
|  | RRT = 0.71 | <LOQ | <LOQ | <LOQ | 0.05 |
|  | RRT = 1.20 | ND | 0.05 | 0.05 | 0.06 |
|  | RRT = 1.49 | 0.05 | 0.06 | 0.05 | 0.06 |
|  | RRT = 1.70 | ND | <LOQ | <LOQ | <LOQ |
|  | Total impurity | 0.05 | 0.11 | 0.10 | 0.17 |
| Formulation 6 | RRT = 0.54 | <LOQ | <LOQ | <LOQ | <LOQ |
|  | RRT = 0.71 | <LOQ | <LOQ | 0.05 | 0.05 |
|  | RRT = 1.20 | ND | 0.05 | 0.06 | 0.05 |
|  | RRT = 1.49 | <LOQ | <LOQ | <LOQ | <LOQ |
|  | RRT = 1.70 | ND | ND | <LOQ | <LOQ |
|  | Total impurity | <LOQ | 0.5 | 0.11 | 0.10 |
| Formulation 8 | RRT = 0.54 | <LOQ | <LOQ | <LOQ | <LOQ |
|  | RRT = 0.71 | <LOQ | <LOQ | 0.05 | 0.05 |
|  | RRT = 1.20 | ND | ND | <LOQ | <LOQ |
|  | RRT = 1.49 | <LOQ | 0.05 | 0.06 | 0.05 |
|  | RRT = 1.70 | ND | ND | <LOQ | <LOQ |
|  | Total impurity | <LOQ | 0.05 | 0.11 | 0.10 |
| Formulation 12 | RRT = 0.54 | ND | <LOQ | <LOQ | 0.05 |
|  | RRT = 0.71 | ND | <LOQ | 0.05 | 0.06 |
|  | RRT = 1.20 | <LOQ | 0.05 | 0.05 | 0.05 |
|  | RRT = 1.49 | <LOQ | <LOQ | <LOQ | <LOQ |
|  | RRT = 1.70 | ND | ND | <LOQ | <LOQ |
|  | Total impurity | <LOQ | 0.05 | 0.10 | 0.16 |
| Formulation 13 | RRT = 0.54 | <LOQ | <LOQ | <LOQ | <LOQ |
|  | RRT = 0.71 | <LOQ | <LOQ | 0.05 | 0.06 |
|  | RRT = 1.20 | ND | <LOQ | <LOQ | 0.05 |
|  | RRT = 1.49 | <LOQ | <LOQ | 0.05 | 0.11 |
|  | RRT = 1.70 | ND | ND | <LOQ | <LOQ |
|  | Total impurity | <LOQ | 0.05 | 0.11 | 0.10 |

Notes:
ND is "not detected";
<LOQ is "<0.05%"
The impurity with RRT = 0.71 was a known impurity A, the others are unknown impurities.

The results of the accelerated stability test indicates that the content of the formulation prepared from API having a particle size more than 89 μm was normal at each time point, and the fluctuation was small and very stability; no obvious increase of the relative substance was observed at 3 months compared to 0 day, which indicated that the product quality was stable and controllable.

Example 6

The inventors further screened the formulations according to the preparation method disclosed in examples 1 to 4, as described in the follows:

Formulation 14 and the amount of components were as shown in table 12

TABLE 12

| | Amount per formulation unit (mg) | Percentage per formulation unit (%) | Amount (g) |
| --- | --- | --- | --- |
| Core tablet: | | | |
| Apixaban | 5.00 | 2.50 | 30.00 |
| Lactose anhydrous | 127.00 | 63.50 | 762.00 |
| Microcrystalline cellulose | 48.00 | 24.00 | 288.00 |
| Croscarmellose sodium | 8.00 | 4.00 | 48.00 |
| Povidone | 6.00 | 3.00 | 36.00 |
| Sodium dodecyl sulfate | 4.00 | 2.00 | 24.00 |
| Magnesium stearate | 2.00 | 1.00 | 12.00 |
| Total | 200.00 | 100.00 | |
| Coating | | | |
| Opadry Y-1-7000 | 6.00 | 3.00 | 36.00 |

Wherein apixaban has a particle size 150 μm.

Glacial acetic acid was weighed based on the final concentration of povidone in glacial acetic acid was 22.5% (g/mL), to the glacial acetic acid were added apixaban having a particle size 150 μm and povidone, the mixture was stirred to dissolve to get a binder solution. Lactose anhydrous, microcrystalline cellulose, croscarmellose sodium and sodium dodecyl sulfate were pre-heated in a fluid bed, when the materials temperature reached 42° C., the binder solution was sprayed to the materials. The materials sprayed with binder solution were dried until the product LOD and residual acetic acid was lower than Quality Standard. The obtained dry granules were sized by 032R screen mesh, and blended with magnesium stearate, the resulting granules were compressed into tablets. The core tablets were coated to get target product.

Formulation 15 and the amount of components were as shown in table 13.

TABLE 13

|  | Amount per formulation unit (mg) | Percentage per formulation unit (%) | Amount (g) |
|---|---|---|---|
| Core tablet: | | | |
| Apixaban | 5.00 | 2.50 | 30.00 |
| Lactose anhydrous | 67.00 | 33.50 | 402.00 |
| Microcrystalline cellulose | 108.00 | 54.00 | 648.00 |
| Croscarmellose sodium | 8.00 | 4.00 | 48.00 |
| Povidone | 6.00 | 3.00 | 36.00 |
| Sodium dodecyl sulfate | 4.00 | 2.00 | 24.00 |
| Magnesium stearate | 2.00 | 1.00 | 12.00 |
| Total | 200.00 | 100.00 | |
| Coating | | | |
| Opadry Y-1-7000 | 6.00 | 3.00 | 36.00 |

Wherein apixaban has a particle size of 200 μm.

Glacial acetic acid was weighed based on the final concentration of povidone in glacial acetic acid was 22.5% (g/mL), to the glacial acetic acid were added apixaban having a particle size of 200 μm and povidone, the mixture was stirred to dissolve to get a binder solution. Lactose anhydrous, microcrystalline cellulose, croscarmellose sodium and sodium dodecyl sulfate were pre-heated in a fluid bed, when the materials temperature reached 42° C., the binder solution was sprayed to the materials. The materials sprayed with binder solution were dried until the product LOD and residual acetic acid was lower than Quality Standard. The obtained dry granules were sized by 032R screen mesh, and blended with magnesium stearate, the resulting granules were compressed into tablets. The core tablets were coated to get the target product.

Formulation 16 and the amount of components were as shown in table 14.

TABLE 14

|  | Amount per formulation unit (mg) | Percentage per formulation unit (%) | Amount (g) |
|---|---|---|---|
| Core tablet: | | | |
| Apixaban | 5.00 | 2.50 | 30.00 |
| Lactose anhydrous | 95.00 | 47.50 | 570.00 |
| Microcrystalline cellulose | 78.00 | 39.00 | 468.00 |
| Croscarmellose sodium | 4.00 | 2.00 | 24.00 |
| Povidone | 16.00 | 8.00 | 96.00 |
| Sodium dodecyl sulfate | 1.00 | 0.50 | 6.00 |
| Magnesium stearate | 1.00 | 0.50 | 6.00 |
| Total | 200.00 | 100.00 | |
| Coating | | | |
| Opadry Y-1-7000 | 6.00 | 3.00 | 36.00 |

Wherein apixaban has a particle size of 200 μm.

Glacial acetic acid was weighed based on the final concentration of povidone in glacial acetic acid was 20% (g/mL), to the glacial acetic acid were added apixaban having a particle size of 200 μm and povidone, the mixture was stirred to dissolve to get a binder solution. Lactose anhydrous, microcrystalline cellulose, croscarmellose sodium and sodium dodecyl sulfate were pre-heated in a fluidized bed, when the materials temperature reached 42° C., the binder solution was sprayed to the materials. The materials sprayed with binder solution were dried until the product LOD and residual acetic acid was lower than Quality Standard. The obtained dry granules were sized by 032R screen mesh, and blended with magnesium stearate, the resulting granules were compressed into tablets. The core tablets were coated to get the target product.

Formulation 17 and the amount of component were as shown in table 15.

TABLE 15

|  | Amount per formulation unit (mg) | Percentage per formulation unit (%) | Amount (g) |
|---|---|---|---|
| Core tablet: | | | |
| Apixaban | 5.00 | 2.50 | 30.00 |
| Lactose anhydrous | 95.00 | 42.00 | 504.00 |
| Microcrystalline cellulose | 78.00 | 39.00 | 468.00 |
| Croscarmellose sodium | 4.00 | 8.00 | 96.00 |
| Povidone | 16.00 | 2.00 | 24.00 |
| Sodium dodecyl sulfate | 1.00 | 4.00 | 48.00 |
| Magnesium stearate | 1.00 | 2.50 | 30.00 |
| Total | 200.00 | 100.00 | |
| Coating | | | |
| Opadry Y-1-7000 | 6.00 | 3.00 | 36.00 |

Wherein apixaban has a particle size of 200 μm.

Glacial acetic acid was weighed based on the final concentration of povidone in glacial acetic acid was 15% (g/mL), to the glacial acetic acid were added apixaban having a particle size of 200 μm and povidone, the mixture was stirred to dissolve to get a binder solution. Lactose anhydrous, microcrystalline cellulose, croscarmellose sodium and sodium dodecyl sulfate were pre-heated in a fluidized bed, when the materials temperature reached 42° C., the binder solution was sprayed to the materials. The materials sprayed with binder solution were dried until the product LOD and residual acetic acid was lower than Quality Standard. The obtained dry granules were sized by 032R screen mesh, and blended with magnesium stearate, the resulting granules were compressed into tablets. The core tablets were coated to get the target product.

Formulation 18 and the amount of component were as shown in table 16.

TABLE 16

|  | Amount per formulation unit (mg) | Percentage per formulation unit (%) | Amount (g) |
|---|---|---|---|
| Core tablet: | | | |
| Apixaban | 2.5 | 2.50 | 30.00 |
| Lactose anhydrous | 48.5 | 48.50 | 582.00 |
| Microcrystalline cellulose | 39.00 | 39.00 | 468.00 |
| Croscarmellose sodium | 4.00 | 4.00 | 48.00 |

TABLE 16-continued

| | Amount per formulation unit (mg) | Percentage per formulation unit (%) | Amount (g) |
|---|---|---|---|
| Povidone | 3.00 | 3.00 | 36.00 |
| Sodium dodecyl sulfate | 2.00 | 2.00 | 24.00 |
| Magnesium stearate | 1.00 | 1.00 | 12.00 |
| Total | 100.00 | 100.00 | |
| Coating | | | |
| Opadry Y-1-7000 | 3 | 3.00 | 36.00 |

Apixaban has a particle size of 300 μm.

Glacial acetic acid was weighed based on the final concentration of povidone in glacial acetic acid was 22.5% (g/mL), to the glacial acetic acid were added apixaban having a particle size of 300 μm and povidone, the mixture was stirred to dissolve to get a binder solution. Lactose anhydrous, microcrystalline cellulose, croscarmellose sodium and sodium dodecyl sulfate were pre-heated in a fluid bed, when the materials temperature reached 42° C., the binder solution was sprayed to the materials. The materials sprayed with binder solution were dried until the product LOD and residual acetic acid was lower than Quality Standard. The obtained dry granules were sized by 032R screen mesh, and blended with magnesium stearate, the resulting granules were compressed into tablets. The core tablets were coated to get the target product.

In this example, the inventors have researched the properties of the apixaban tablets obtained from example 6.

1. Dissolution Test

The dissolution conditions were the same as Example 1, wherein the dissolution curves (%) of formulations 14 to 18 are listed in table 17.

TABLE 17 the dissolution curves (%) of formulations 14 to 18.

| Formulation | 5 min | 10 min | 15 min | 20 min | 30 min | 45 min | 60 min |
|---|---|---|---|---|---|---|---|
| Formulation 14 | 38 | 81 | 94 | 98 | 98 | 99 | 98 |
| Formulation 15 | 39 | 85 | 97 | 98 | 98 | 99 | 98 |
| Formulation 16 | 37 | 82 | 93 | 98 | 100 | 101 | 101 |
| Formulation 17 | 33 | 64 | 90 | 93 | 97 | 99 | 100 |
| Formulation 18 | 41 | 83 | 96 | 101 | 101 | 102 | 102 |

2. Stability Test

TABLE 18 stability data of formulation 18.

| | | 0 d (%) | 1 monthes (%) | 3 monthes (%) | 6 monthes (%) | Standard limit (%) |
|---|---|---|---|---|---|---|
| Known impurity | Impurity A (RRT = 0.71) | <LOQ | <LOQ | <LOQ | 0.05 | ≤0.5 |
| Unknown impurities | RRT = 0.54 | <LOQ | <LOQ | <LOQ | <LOQ | ≤0.2 |
| | RRT = 1.20 | ND | <LOQ | 0.05 | 0.06 | ≤0.2 |
| | RRT = 1.49 | 0.05 | 0.05 | 0.05 | 0.06 | ≤0.2 |
| | RRT = 1.70 | ND | ND | <LOQ | <LOQ | ≤0.2 |
| Total impurity | | 0.05 | 0.05 | 0.10 | 0.17 | ≤1.0 |
| Content | | 101.7 | 100.6 | 101.3 | 101.1 | 90.00-110.00 |

Notes:
ND is "not detected";
<LOQ is "<0.05%"

Listed in table 17 and table 18, the apixaban tablets prepared by the optimization method screened from examples 1 to 4, such as formulations 14 to 18, have good stability and faster dissolution rate, the dissolution was more than and equal to 90% at 15 min.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments or examples of the specification or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. An apixaban solid composition comprising apixaban having a particle size $D_{90}$ more than 89 μm, wherein the apixaban is dissolved in a wetting agent, wherein the wetting agent is an acidic substance or an organic solvent.

2. The apixaban solid composition of claim 1, wherein the apixaban has a particle size $D_{90}$ between 100 μm and 550 μm.

3. The apixaban solid composition of claim 1, wherein the apixaban solid composition further comprises a binder.

4. The apixaban solid composition of claim 3, wherein the binder is povidone; or wherein the binder has a content of 2.00% to 8.00% by weight, based on the total weight of the apixaban solid composition.

5. The apixaban solid composition of claim 3, wherein the binder is provided in dissolved form in an acidic substance or an organic solvent.

6. The apixaban solid composition of claim 3 further comprising a filler, a disintegrant, a surfactant and a lubricant.

7. The apixaban solid composition of claim 6, wherein the filler is corn starch, pregelatinized starch, complex starch, lactose anhydrous, lactose monohydrate, microcrystalline cellulose, methylcellulose, hydroxy propyl cellulose, hydroxy propyl methyl cellulose, mannitol, maltitol, inositol, xylitol, lactitol or a combination thereof.

8. The apixaban solid composition of claim 6, wherein the filler is a mixture of lactose anhydrous and microcrystalline cellulose, and wherein the content of the lactose anhydrous is from 33.50% to 63.50% and the content of the microcrystalline cellulose is from 24.00% to 54.00% by weight, based on the total weight of the apixaban solid composition.

9. The apixaban solid composition of claim 6, wherein the disintegrant is croscarmellose sodium; or wherein the disintegrant is croscarmellose sodium having a content from 2.00% to 8.00% by weight, based on the total weight of the apixaban solid composition.

10. The apixaban solid composition of claim 6, wherein the surfactant is sodium dodecyl sulfate; or wherein the surfactant is sodium dodecyl sulfate having a content from 0.50% to 4.00% by weight, based on the total weight of the apixaban solid composition.

11. The apixaban solid composition of claim 6, wherein the lubricant is magnesium stearate; or wherein the lubricant is magnesium stearate having a content from 0.50% to 2.50% by weight, based on the total weight of the apixaban solid composition.

12. An apixaban solid composition comprising 2.50 parts by weight of apixaban, 33.50 to 63.50 parts by weight of lactose anhydrous, 24.00 to 54.00 parts by weight of microcrystalline cellulose, 2.00 to 8.00 parts by weight of croscarmellose sodium, 2.00 to 8.00 parts by weight of povidone, 0.50 to 4.00 parts by weight of sodium dodecyl sulfate and 0.50 to 2.50 parts by weight of magnesium stearate, wherein the apixaban has a particle size D90 more than 89 μm or between 100 μm and 550 μm, wherein the apixaban solid composition further comprises a wetting agent, and wherein the wetting agent is an acidic substance or an organic solvent.

13. The apixaban solid composition of claim 12, wherein the apixaban solid composition comprises 2.50% of apixaban, 48.50% of lactose anhydrous, 39.00% of microcrystalline cellulose, 4.00% of croscarmellose sodium, 3.00% of povidone, 2.00% of sodium dodecyl sulfate and 1.00% of magnesium stearate by weight, based on the total weight of the apixaban solid composition, and wherein the apixaban has a particle size $D_{90}$ more than 89 μm; or wherein the apixaban solid composition comprises 2.50% of apixaban, 63.50% of lactose anhydrous, 24.00% of microcrystalline cellulose, 4.00% of croscarmellose sodium, 3.00% of povidone, 2.00% of sodium dodecyl sulfate and 1.00% of magnesium stearate by weight, based on the total weight of the apixaban solid composition, and wherein the apixaban has a particle size $D_{90}$ more than 89 μm; or wherein the apixaban solid composition comprises 2.50% of apixaban, 33.50% of lactose anhydrous, 54.00% of microcrystalline cellulose, 4.00% of croscarmellose sodium, 3.00% of povidone, 2.00% of sodium dodecyl sulfate and 1.00% of magnesium stearate by weight, based on the total weight of the apixaban solid composition, and wherein the apixaban has a particle size $D_{90}$ more than 89 μm; or wherein the apixaban solid composition comprises 2.50% of apixaban, 47.50% of lactose anhydrous, 39.00% of microcrystalline cellulose, 2.00% of croscarmellose sodium, 8.00% of povidone, 0.50% of sodium dodecyl sulfate and 0.50% of magnesium stearate by weight, based on the total weight of the apixaban solid composition, and wherein the apixaban has a particle size $D_{90}$ more than 89 μm; or wherein the apixaban solid composition comprises 2.50% of apixaban, 42.00% of lactose anhydrous, 39.00% of microcrystalline cellulose, 8.00% of croscarmellose sodium, 2.00% of povidone, 4.00% of sodium dodecyl sulfate and 2.50% of magnesium stearate by weight, based on the total weight of the apixaban solid composition, and wherein the apixaban has a particle size $D_{90}$ more than 89 μm.

14. A method of preparing an apixaban composition comprising:
granulating apixaban by using a wet granulation method, and dissolving apixaban in a wetting agent, wherein the wetting agent is an acidic substance or an organic solvent, and wherein the apixaban has a particle size $D_{90}$ more than 89 μm.

15. The method of claim 14, wherein the wet granulation method comprises dissolving apixaban and a binder in the wetting agent to get a binder solution.

16. The method of claim 15, wherein the binder is povidone; or wherein the content of the binder is from 0.02 g/mL to 0.5 g/mL in the wetting agent.

17. The method of claim 14, wherein the particle size $D_{90}$ of the apixaban is between 100 μm and 550 μm.

18. The method of claim 15 further comprising:
preheating a filler, a disintegrant and a surfactant in a fluid-bed, wherein the temperature is from 35° C. to 50° C. after preheating;
spraying the binder solution to the preheated product, wherein the spraying is carried out under an atomizing pressure from 0.5 bar to 2.0 bar and at a spray speed from 3.0 g/min to 20.0 g/min;
drying the preheated product sprayed with the binder solution to get dry granules;
sizing the dry granules; and
blending a lubricant with the sized granules.

19. The method of claim 15 further comprising:
pre-blending a filler, a disintegrant and a surfactant in a high shear wet granulator;
spraying the binder solution to the pre-blended product to get wet granules, wherein the spraying is carried out at a spraying speed from 5 g/min to 60 g/min;
drying the wet granules in a fluid-bed to get dry granules;
sizing the dry granules; and
blending a lubricant with the sized granules.

20. The method of claim 14 further comprising compressing the blend product into tablets and coating the tablets.

21. The apixaban solid composition of claim 1, wherein the apixaban solid composition is obtained by using a wet granulation method.

22. The apixaban solid composition of claim 1, wherein the apixaban solid composition is in a form of immediate release tablets.

23. The apixaban solid composition of claim 1, wherein the acidic substance is formic acid, acetic acid, a combination thereof, or a mixture thereof with water; wherein the organic solvent is DMSO a combination thereof, or a mixture thereof with water.

24. The apixaban solid composition of claim 5, wherein the acidic substance is acetic acid; or wherein the content of the binder is from 0.02 g/mL to 0.5 g/mL in acetic acid.

* * * * *